(12) United States Patent
Henrich et al.

(10) Patent No.: US 7,247,733 B2
(45) Date of Patent: Jul. 24, 2007

(54) PROCESS FOR PREPARING NUCLEAR-FLUORINATED AROMATICS

(75) Inventors: Marielouise Henrich, Leverkusen (DE); Albrecht Marhold, Leverkusen (DE); Alexander Kolomeitsev, Kiew (UA); Gerd Röschenthaler, Bremen (DE)

(73) Assignee: Lanxess Deutschland GmbH, Leverkusen (DE)

( * ) Notice: Subject to any disclaimer, the term of this patent is extended or adjusted under 35 U.S.C. 154(b) by 271 days.

(21) Appl. No.: 11/148,695

(22) Filed: Jun. 9, 2005

(65) Prior Publication Data

US 2005/0228201 A1  Oct. 13, 2005

Related U.S. Application Data

(62) Division of application No. 10/171,004, filed on Jun. 12, 2002, now Pat. No. 7,091,362.

(30) Foreign Application Priority Data

Jun. 15, 2001  (DE) ................. 101 29 057

(51) Int. Cl.
  *C07D 233/48* (2006.01)
  *C07C 22/04* (2006.01)
(52) U.S. Cl. ................... 548/331.5; 570/145
(58) Field of Classification Search ............ 548/331.5; 570/145
  See application file for complete search history.

(56) References Cited

U.S. PATENT DOCUMENTS

| | | | |
|---|---|---|---|
| 4,287,374 A | 9/1981 | North | 568/937 |
| 4,973,771 A | 11/1990 | Cantrell | 568/937 |
| 5,041,683 A * | 8/1991 | Marhold et al. | 568/425 |
| 5,627,291 A | 5/1997 | Fischer | 549/507 |
| 5,667,956 A | 9/1997 | Missfeldt et al. | 430/600 |
| 6,103,659 A | 8/2000 | Pasenok et al. | 502/208 |
| 6,184,425 B1 | 2/2001 | Kolomeitsev et al. | 570/170 |

FOREIGN PATENT DOCUMENTS

EP  0 791 600  8/1997

WO  87/04149  7/1987

OTHER PUBLICATIONS

Synthesis, Mar. 1979, pp. 215-216, "2-Azavinamidinium-Salze und ihre Umwandlung in Dialkylamino-thiazole und -imidazole", R. Gompper and C.S. Schneider.
Angewandte Chemie, 104, (month unavailable) 1992, pp. 684, "Eine sichere Synthese von Diphosphazenium-Salzen", Von Reinhard Link und Reinhard Schwesinger.
Hamed A et al: "2-Azoniaalene Salts From 8-11 the Reaction of Chlorocarbenium Salts with N-Silylimines" SYNTHESIS, Nr. 5, 1989, Seiten 400-2, XP001083979 ISSN: 0039-7881 Verbindung 4a.
Marchenko A et al: "N—Chlorophosphorimidic triamides" Journal Of General Chemistry Of The USSR (English translation), Bd. 53, Nr. 3, 1983, Seiten 583-9, XP001087779 ISSN: 0022-1279 Seite 584; Tabelle 2.
Dorta et al: "The IrCl(Diphosphine) !2/Fluoride System. Developing Catalytic Asymmetric Olefin Hydroamination" Journal Of The American Chemical Society, American Chemical Society, Washington, DC, US, Bd. 119, Nr. 44, Nov. 5, 1997, Seiten 10857-10858, XP0021110586 ISSN: 0002-7863 Referenz (15).
Schwesinger R et al: "Stable Phosphazenium Ions in Synthesis—an Easily Accessible, Extremely Reactive "Naked" Fluoride Salt" Angewandte Chemie, International Edition, Verlag Chemie, Weinheim, DE, Bd. 30, Nr. 10, 1991, Seiten 1372-1375, XP002941731 ISSN: 0570-0833 Schema 1.
Schwesinger R et al: "Extremely strong, uncharged auxiliary bases; monomeric and polymer-supported polyaminophosphazenes (P2-P5)" Liebigs Annalen, 1996, Seiten 1055-1081, XP002139767 ISSN:0947-03440 Seite 1066, rechte Spalte, Zeile 28—Zeile 56 Seite 1079, linke Spalte, Zeile 58—Seite 1079, rechte Spalte, Zeile 2.

* cited by examiner

*Primary Examiner*—Kamal Saeed
(74) *Attorney, Agent, or Firm*—Michael A. Miller

(57) ABSTRACT

The present invention relates to the preparation of nuclear-fluorinated aromatics by reacting, with a fluoride at 40 to 260° C., an aromatic compound substituted at the nucleus with halogen that is exchangeable for fluorine in the presence of at least one compound of the formula (I)

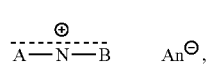

where A, B, and An$^\ominus$ have the meanings specified in the disclosure.

10 Claims, No Drawings

PROCESS FOR PREPARING NUCLEAR-FLUORINATED AROMATICS

This application is a divisional of U.S. application Ser. No. 10/171,004 filed Jun. 12, 2002, now U.S. Pat. No. 7,091,362 and claims priority to Germany 10129057.8, filed on Jun. 15, 2001 the contents of which are incorporated herein.

BACKGROUND OF THE INVENTION

The present invention relates to an improved process for preparing nuclear-fluorinated aromatics by a halogen exchange reaction (halex reaction) in the presence of a catalyst.

Nuclear-fluorinated aromatics are important intermediates for preparing biologically active substances for pharmaceutical and agrochemical applications.

It is known to carry out halex reactions in aprotic, strongly polar solvents using metal fluorides at elevated temperature and in the presence of alkylammonium or alkylphosphonium salts (U.S. Pat. No. 4,287,374), pyridinium salts (WO 87/04149), crown ethers (DE-A 197 02 282), or tetraamidophosphonium salts (WO 98/05610). Disadvantages in reactions of this type are, particularly when weakly activated aromatics are used, the high reaction temperatures and long reaction times that are required. This leads to high energy consumption and low space-time yields. The high reaction temperatures frequently lead to the formation of unwanted by-products and decomposition products. In addition large amounts of expensive solvents are required.

Furthermore, for example, the tetraamidophosphonium salts (WO 98/05610) are extremely toxic.

The requirement therefore still exists for a process for preparing nuclear-fluorinated aromatics by a halex reaction in which less energy is consumed, higher chemical and space-time yields are possible, and solvents may optionally be avoided.

SUMMARY OF THE INVENTION

A process has now been found for preparing nuclear-fluorinated aromatics comprising reacting, at 40 to 260° C.,
(1) an aromatic compound substituted at the nucleus with halogen that is exchangeable for fluorine, with (2) a fluoride, in the presence of
(3) at least one compound of the formula (I),

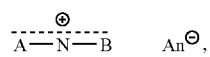   $An^\ominus$, (I)

where
A is a radical of the formula (II) or (III)

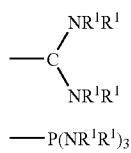

and

B independently of A is a radical of the formula (II), (III), (IV), or (IVa)

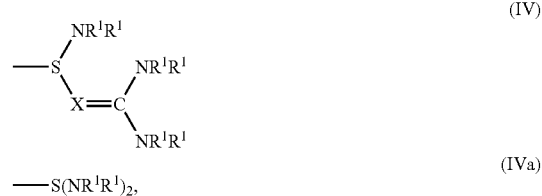

where the individual $R^1$ are identical or different and are each unbranched or branched $C_1$-$C_{10}$ alkyl, unbranched or branched $C_2$-$C_{10}$ alkylene, or $C_6$-$C_{12}$ aryl, where one or more $NR^1R^1$ groups can also be a 3- to 7-membered saturated or unsaturated ring that is formed from the nitrogen atom, the remainder of the ring atoms being carbon atoms, and where the radical of the formula (II) and the

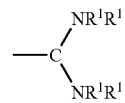

group in formula (IV) can also be the radical of a saturated or unsaturated 4- to 8-membered ring that contains the two nitrogen atoms, the remainder of the ring atoms being carbon atoms, X is nitrogen or phosphorus, and $An^\ominus$ is one equivalent of an anion.

DETAILED DESCRIPTION OF THE INVENTION

Preferably, the two $R^1$ radicals bound to the same nitrogen atom are identical.

Preferably, the radicals $R^1$ are methyl, ethyl, propyl, or butyl, or an $NR^1R^1$ group is a 5- to 7-membered saturated or unsaturated ring that is formed from one nitrogen atom, the remainder of the ring atoms being carbon atoms, or the radical of formula (II) or the

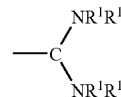

group in formula (IV) is a saturated 5- or 7-membered ring that contains the two nitrogen atoms, the remainder of the ring atoms being carbon atoms; X is nitrogen; and $An^\ominus$ is chloride, bromide, $(CH_3)_3SiF_2^\ominus$, $HF_2^\ominus$, $H_2F_2^\ominus$, tetrafluoroborate, hexafluorophosphate, carbonate, or sulfate.

Very particularly preferred compounds of the formula (I) are those corresponding to the formulas (V) to (IX).

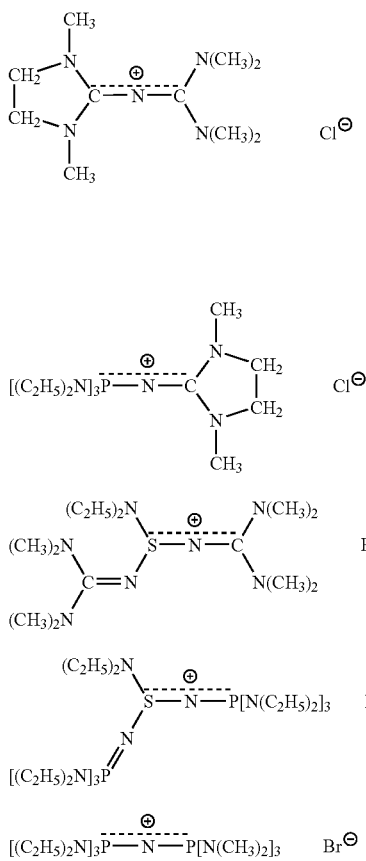

It is an advantage of the inventive process that it can be applied to a great number of aromatic compounds substituted with halogen that is exchangeable for fluorine, and thus a great number of nuclear-fluorinated aromatics can be prepared. The halogen that is exchangeable for fluorine can be, for example, chlorine and/or bromine. Preference is given here to chlorine.

For example, using the inventive process, advantageously, nuclear-fluorinated aromatics of the formula (X) can be prepared $$R^2_x ArF_w Cl_{(y-w)} R^3_z \quad (X),$$

where

R$^2$ independently of one another are each F, Cl, Br, NO$_2$, CN, CF$_3$, CCl$_3$, CHO, OCF$_3$, SCF$_3$, COR$^4$, COOR$^4$, COY, or SO$_2$Y, where R$^4$ is C$_1$-C$_{10}$ alkyl and Y=F, Cl, Br or CF$_3$, R$^3$ independently of one another are each hydrogen or an unbranched or branched C$_1$-C$_{10}$ alkyl or C$_1$-C$_{10}$ alkoxy radical, Ar is an aromatic or heteroaromatic radical having a total of 6 to 10 ring atoms, where the ring atoms are only carbon atoms or alternatively are carbon atoms plus 1 to 3 heteroatoms selected from the group consisting of nitrogen, oxygen, and sulfur, x is an integer from 1 to 3, w is an integer from 1 to y, y is an integer from 1 to 5, and z is zero or an integer from 1 to 5, where the total x+y+z equals the number of all substitutable valencies on the radical Ar.

Preferably, suitable aromatic compounds substituted with halogen that is exchangeable for fluorine are those corresponding to the formula (XI)

$$R^2_x ArCl_y R^3_z \quad (XI),$$

where R$^2$, R$^3$, Ar, x, y, and z have the meanings specified for formula (X).

Preferably, in the formulas (X) and (XI)

R$^2$ independently of one another are each Cl, NO$_2$, CN, CF$_3$, COCl, or CHO, R$^3$ independently of one another are each hydrogen, methyl, ethyl, methoxy, or ethoxy, Ar is a phenyl or pyridyl radical, x is 1 or 2, w is 1 or 2, y is an integer from 1 to 4, and z is zero or 1.

Examples of compounds of the formula (XI) are 2,3,4,5-tetrachloro-benzotrifluoride, 4-chloronitrobenzene, 3,4-dichlorobenzonitrile, 2,6-di-chlorobenzonitrile, 2,4-dichlorobenzaldehyde, 3,4,5-trichloropyridine, 4-chlorobenzaldehyde, 3,4-dichlorobenzotrifluoride, 1,2,3-trichlorobenzene and 2,6-dichlorobenzoyl chloride.

Fluorides that are suitable for an exchange of halogen for fluorine are, for example, alkali metal fluorides, alkaline earth metal fluorides, and ammonium fluorides. Preference is given to potassium fluoride, sodium fluoride, calcium fluoride, and ammonium fluoride and mixtures thereof among one another and mixtures thereof with lithium fluoride, rubidium fluoride, and/or cesium fluoride.

Based on 1 mol of halogen that is bound to the nucleus of an aromatic compound and is to be exchanged for fluorine, for example, 0.001 to 0.5 mol (preferably 0.01 to 0.02 mol) of one or more compounds of the formula (I) and, for example, 0.8 to 2 equivalents (preferably 1.1 to 1.3 equivalents) of one or more fluorides can be used.

The inventive process is preferably carried out at temperatures in the range 70 to 220° C. Particular preference is given to 90 to 200° C.

The inventive process can be carried out in the presence or absence of solvents. Particularly for the conversion of polychlorinated benzotrifluorides to fluorinated and chlorinated benzotrifluorides and/or to polyfluorinated benzotrifluorides, a solvent is not necessary. If it is wished to use a solvent, dipolar aprotic and nonpolar aprotic solvents, for example, are suitable. Suitable dipolar aprotic solvents are, for example, dimethyl sulfoxide, sulfolane, dimethylformamide, dimethylacetamide, 1,3-dimethylimidazolin-2-one, N-methylpyrrolidone, acetonitrile, and benzonitrile. Suitable nonpolar aprotic solvents are, for example, benzene, toluene, chlorobenzene, dichlorobenzenes, chlorotoluenes, and chloro-alkanes such as dichloromethane.

Nonpolar aprotic and dipolar aprotic solvents can be used in any amounts, for example, in amounts of 0.1 to 500% by weight (preferably in amounts of 0.2 to 40% by weight), in each case based on the aromatic compound that is substituted with halogen exchangeable for fluorine.

Mixtures of solvents can also be used, in which case it is preferred to use those solvent mixtures that contain 50% by weight or more of dipolar aprotic solvents.

The reaction time in the inventive process can be, for example, in the range of from 2 to 36 hours.

The inventive process can be carried out under reduced, atmospheric, or elevated pressure. Preferably, atmospheric pressure or slightly elevated pressure (for example, 1 to 6 bar) is employed.

In principle, the compounds of formula (I) can be handled in the presence or absence of atmospheric oxygen. However, it is preferred to handle the compounds of the formula (I) under protective gas and to carry out the inventive process under protective gas. Suitable protective gases are, for example, nitrogen and argon.

The inventive process may be carried out batchwise or continuously.

To work up the reaction mixture that is present after carrying out the inventive process, a procedure can be followed, for example, in such a manner that the reaction mixture, after cooling, is mixed with water, the organic phase that forms is separated off, and the separated organic phase is subjected to fractional distillation at reduced pressure. The reaction mixture that is present after carrying out the inventive process can also be subjected directly to distillation.

In addition, a solvent can be added to the reaction mixture, solid constituents can be separated off by filtration, and the filtrate can be distilled under reduced pressure. It is also possible to employ other workup methods.

The compounds of the formula (I) in which A and B are identical and each correspond to a radical of the formulas (II) or (III) can be prepared in a known manner or by similar methods thereto (see Synthesis 1979, 215-216, and Angewandte Chemie, 104, 864, 1992)).

The present invention also relates to a process for preparing any of the compounds of the formula (I) comprising (a) reacting
(i) a compound of the formula

[A-An']$^{\oplus}$ An$^{\ominus}$         (XII), where
A has the meaning specified for formula (I) or corresponds to the formula (IVa),
An' is chlorine or bromine, and
An$^{\ominus}$ is one equivalent of an anion,
with
(ii) a compound of the formula (XIII)

HN=A'         (XIII), where
A' with respect to the arrangement of the atoms has the meaning specified for A of formula (I) but is double-bonded, and
(2) adding a base.

An example of such a reaction is

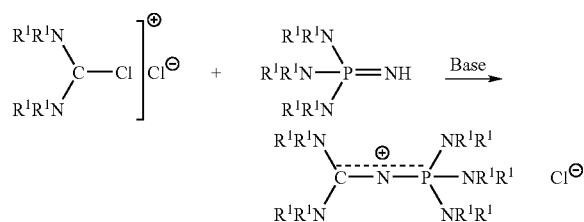

In the formulas (XII) and (XIII), A and An$^{\ominus}$ preferably have the meanings specified as preferred for formula (I), An' is chlorine or bromine, and A' has the preferred meaning specified for A for formula (I) but is double-bonded.

Suitable bases are, for example, alkoxides, tertiary amines, and compounds of the formula (XIII) used in excess. Preference is given to sodium alkoxides and potassium alkoxides of unbranched or branched $C_1$-$C_4$ alkyl alcohols and tri($C_1$-$C_{10}$ alkyl)amines. Particular preference is given to sodium methoxide, sodium ethoxide, and triethylamine. If compounds of the formula (XIII) are available fairly inexpensively (for example, if this is the case for tetraalkylguanidine), then excesses of compounds of the formula (XIII) as bases are also particularly preferred.

Compounds of the formula (XII) can be prepared in a known manner or in a similar manner thereto, for example, by halogenating the corresponding urea, for example, using $SOCl_2$, $(COCl)_2$ or $COCl_2$, or by reacting phosphorus pentachloride with a secondary amine such as diethylamine, or by halogenating a compound of the type $(R_2N)_2S$ with, for example, bromine.

Compounds of the formula (XIII) can be prepared in a known manner or using similar methods thereto, for example, by reacting phosphorus pentachloride with a secondary amine, ammonia, and an alkali metal hydroxide solution, for example, according to the following equation:

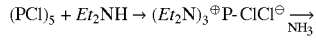
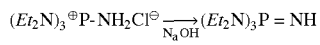

where $Et$ = ethyl

The compounds of the formula (XIII) can also be used in the form of their hydrohalides, as frequently first occur during their preparation.

In the inventive process for preparing compounds of the formula (I), a compound of the formula (XIII) can be used, for example, in an amount of 0.8 to 3 mol (preferably 1 to 2 mol), based on the compound of the formula (XII).

The compounds of the formulas (XII) and (XIII) can be reacted, for example, at temperatures in the range −80 to +70° C., preferably in the range −70 to +20° C. Within these temperature ranges it is advantageous to employ relatively high temperatures for the formation of N—C bonds, medium temperatures for the formation of N—P bonds, and relatively low temperatures for the formation of N—S bonds.

Suitable solvents are, for example, chlorinated aliphatic and aromatic hydrocarbons, ethers, in particular cyclic ethers, nitriles, amides, sulfoxides, and aliphatic and aromatic hydrocarbons. Preference is given to methylene chloride, 1,2-dichloroethane, tetrahydrofuran, dioxane, toluene, acetonitrile, dimethylformamide, and dimethyl sulfoxide. Care must be taken in selection of the solvent so that it does not convert into the solid state under the reaction conditions.

The reaction of a compound of the formula (XII) with a compound of the formula (XIII) is generally complete after 0.5 to 24 hours, frequently after 4 to 12 hours. Then, the base can be added, for example, in an amount of 1 to 1.2 equivalents, based on one mole of the compound (XII). When, as base, an excess of compound (XIII) is used, then, for example, in total 2 to 2.2 mol of the compound of the formula (XIII), based on the compound (XII), can be used. Suitable solvents for alkoxides and tertiary amines are particularly alcohols. Excess compounds of the formula (XIII) do not require additional solvent. The base can be added, for example, at −50 to +40° C., preferably at −10 to +10° C. It is advantageous to stir the reaction mixture further after completion of the addition of base for some time (for example, 0.5 to 1 hour) in the specified temperature range.

To work up the reaction mixture, for example, after removing the solid constituents, solvent can be taken off and the product then present can be purified for example by extraction with a solvent, for example, a ketone, ether, or hydrocarbon. Other potential workup methods are also conceivable.

It is advantageous to carry out the synthesis and workup of compounds of the formula (I) under a protective gas atmosphere, for example, under nitrogen or argon.

The compounds of the formula (I) prepared according to the invention are suitable for use as catalyst for halex reactions as they are obtained after the above-described workup. In some cases it has been observed that, in the inventive preparation of compounds of the formula (I), mixtures of two or more individual compounds corresponding to the formula (I) are produced. Such mixtures of substances are also suitable as catalysts for halex reactions. These mixtures of substances can be, for example, those containing compounds of the formula (I) where A is formula (II) and B is formula (IV) and formula (IVa) or the compounds of the formula (I) where A is formula (III) and B is formula (IV) and formula (IVa). The inventive process for preparing compounds of the formula (I) below provides a universally applicable process by which compounds of the formula (I) are accessible in a simple and efficient manner.

The invention further relates to compounds of the formula (I)

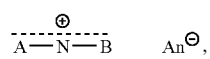   $An^{\ominus}$,   (I)

where
A is a radical of the formula (II) or (III)

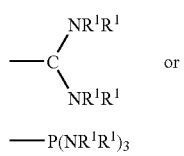   or   (II)

—P(NR$^1$R$^1$)$_3$   (III)

and
B independently of A is a radical of the formula (IV) or (IVa)

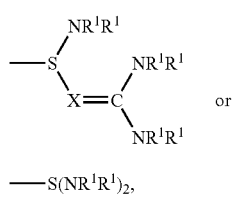   or   (IV)

—S(NR$^1$R$^1$)$_2$,   (IVa)

where the individual R$^1$ are identical or different and are each an unbranched or branched C$_1$-C$_{10}$ alkyl, unbranched or branched C$_2$-C$_{10}$ alkylene, or C$_6$-C$_{12}$ aryl, where one or more NR$^1$R$^1$ groups can also be a 3- to 7-membered, saturated or unsaturated ring that is formed from one nitrogen atom, the remainder of the ring atoms being carbon atoms, and
where the radical of the formula (II) and the

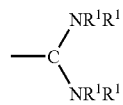

group in formula (IV) can also be the radical of a saturated or unsaturated 4- to 8-membered ring that contains two nitrogen atoms, the remainder of the ring atoms being carbon atoms,
X is nitrogen or phosphorus, and
An$^{\ominus}$ is one equivalent of an anion.

Preferably the radicals R$^1$ are methyl, ethyl, propyl, or butyl, or an NR$^1$R$^1$ group is a 5- to 7-membered saturated or unsaturated ring that is formed from one nitrogen atom, the remainder of the ring atoms being carbon atoms, or the radical of the formula (II) or the

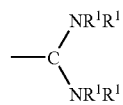

group in formula (IV) is a saturated 5- or 7-membered ring that contains two nitrogen atoms, the remainder of the ring atoms being carbon atoms; X is nitrogen; and An$^{\ominus}$ is chloride, bromide, (CH$_3$)$_3$SiF$_2^{\ominus}$, HF$_2^{\ominus}$, H$_2$F$_2^{\ominus}$, tetrafluoroborate, hexafluorophosphate, carbonate, or sulfate.

Particular preference is given to diethylaminobis(tetramethyl-guanidino)sulfonium bromide [formula (VII)] and diethylaminobis[tris-(diethylamino)phosphazenyl]sulfonium bromide [formula (VIII)].

These inventive compounds are accessible, as described, via the inventive preparation process.

The inventive process for preparing nuclear-fluorinated aromatics uses more effective catalysts, requires less energy, makes possible higher chemical and space-time yields, and can if appropriate be carried out without addition of solvent. Frequently, in this inventive process, fewer toxic compounds must be handled than in the process of the prior art. Even if, in a specific individual case, only one or two of these advantages should be realizable, this is a considerably improved process compared with the prior art.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

Inventive Preparation of 4-nitrofluorobenzene 157 g of 4-nitrochlorobenzene, 200 g of dimethylsulfoxide, 62.7 g of potassium fluoride, and 2.49 g of (N,N-dimethylimidazolidino)tetramethyl-guanidinium chloride were placed in a 1 liter four-neck flask equipped with thermometer, anchor stirrer, and reflux condenser with bubble counter. The mixture was heated with stirring to 170° C. and kept at this temperature for 5 hours. The reaction mixture was then cooled to room temperature, water was added at a volumetric ratio of 1:1, the phases that formed were separated, and, from the organic phase, by fractional distillation at reduced pressure, 4-nitrofluorobenzene was obtained in a yield of 96% of theory.

Comparative Example 1

Preparation of 4-Nitrofluorobenzene According to the Prior Art

A procedure was followed as in Example 1, but instead of (N,N-dimethylimidazolidino)tetramethylguanidinium chloride, the same molar amount of tetrakis(diethylamino)phosphonium bromide was used. 4-Nitrofluorobenzene was obtained after a 6-hour reaction time in a yield of 93% of theory.

Comparative Example 2

Preparation of 4-nitrofluorobenzene According to the Prior Art

A procedure was followed as in Example 1, but instead of (N,N-dimethylimidazolidino)tetramethylguanidinium chloride, the same molar amount of tetraphenylphosphonium bromide was added. 4-Nitro-fluorobenzene was obtained after a 6-hour reaction time in a yield of 89% of theory.

Example 2

Inventive Preparation of 3-chloro4-fluorobenzonitrile 172 g of 3,4-dichlorobenzonitrile, 200 g of dimethylsulfoxide, 69.6 g of potassium fluoride, and 3.95 g of (N,N-dimethylimidazolidino)tris-(diethylamino)phosphazenium chloride were placed in a 1 liter four-neck flask equipped with anchor stirrer, thermometer, and reflux condenser with bubble counter. The mixture was then heated with stirring to 170° C. and this temperature was maintained for 6 hours. The mixture was then cooled to room temperature, water was added to the reaction mixture in a volumetric ratio of 1:1, and the 3-chloro4-fluorobenzonitrile that precipitated was isolated by filtration, washing, and drying. 3-Chloro4-fluorobenzo-nitrile was obtained in a yield of 92% of theory.

Comparative Example 3

Preparation of 3-chloro-4-fluorobenzonitrile According to the Prior Art

The procedure was followed as in Example 2, but the catalyst was an equivalent molar amount of tetraphenylphosphonium bromide. 3-Chloro4-fluorobenzonitrile was obtained in a yield of 81% of theory.

Example 3

Inventive Preparation of 4-fluorobenzonitrile 200 g of 4-chlorobenzonitrile, 101.4 g of potassium fluoride, 25 g of dimethyl sulfoxide, and 5.60 g of (N,N-dimethylimidazolidino)tetramethyl-guanidinium chloride were placed in a 1 liter 4-neck flask equipped with anchor stirrer, thermometer, and reflux condenser with bubble counter. The mixture was then heated with stirring to 180° C. and this temperature was maintained for 16 hours. The mixture was then cooled to room temperature, water was added to the reaction mixture in a volumetric ratio of 1:1, and the mixture was extracted with diethyl ether. After washing, concentration, and drying the separated organic phase, 4-fluorobenzo-nitrile was isolated in a yield of 75%.

Comparative Example 4

Preparation of 4-fluorobenzonitrile According to the Prior Art 25.3 9 of potassium fluoride in 70 ml of sulfolane were placed in a 250 ml 4-neck flask equipped with anchor stirrer, thermometer, and reflux condenser with bubble counter, and the mixture was stirred for 1 hour at 100° C. The reflux condenser was then removed, a distillation head was attached instead, and 20 ml of sulfolane were distilled off under reduced pressure. The apparatus was then charged with nitrogen, the reflux condenser was again attached, and 50 g of 4-chlorobenzonitrile and 1.52 g of tetraphenylphosphonium bromide were added. The mixture was then heated with stirring to 180° C. and this temperature was maintained for 6 hours. It was then found by gas-chromatographic analysis that only 2% of the 4-chlorobenzonitrile used had been converted to 4-fluorobenzo-nitrile.

Example 4

Inventive Preparation of 2,4-difluorobenzoyl fluoride 100 g of 2,4-dichlorobenzoyl chloride, 100 g of N,N-dimethylimid-azolidin-2-one, 94.3 g of potassium fluoride, and 1.78 g of (N,N-dimethyl-imidazolidino)tetramethylguanidinium chloride were placed in a 1 liter 4-neck flask equipped with anchor stirrer, thermometer, and reflux condenser with bubble counter. The mixture was then heated with stirring to 180° C. and this temperature was maintained for 24 hours. The mixture was then cooled to room temperature, dichloromethane was added to the reaction mixture in a volumetric ratio of 1:1, and the mixture was filtered. The solvent was removed from the filtrate and the remainder was subjected to fractional distillation. 2,4-Difluorobenzoyl fluoride was obtained in 75% yield.

Comparative Example 5

Preparation of 2,4-difluorobenzoyl fluoride According to the Prior Art 200 g of 2,4-chlorobenzoyl chloride and 200 g of sulfolane were placed in an autoclave and heated for 9 hours with stirring at 200° C. The mixture was then allowed to cool to room temperature and depressurized and the product was distilled off directly from the reaction mixture. In this manner 2,4-difluorobenzoyl fluoride was obtained in 35% yield.

Example 5

Inventive Preparation of Tetrafluorobenzotrifluoride (a) 400 g of tetrachlorobenzotrifluoride, 212 g of potassium fluoride, 5 g of (N,N-dimethylimidazolidino)tetramethylguanidinium chloride, and 2 g of dichloromethane were placed in a 1 liter autoclave and heated with stirring for 8 hours at 200° C. The mixture was then cooled to room temperature, the precipitated salts were filtered off, and the filtrate was analyzed by gas chromatography. The analytical results can be seen in Table 1.

(b) The filtrate from substep (a) was placed in a 1 liter autoclave together with 6.3 g of (N,N-dimethylimidazolidino)tetramethylguanidinium chloride and 193.5 g of potassium fluoride and heated for 32 hours at 200° C. The mixture was then cooled to room temperature, the autoclave was depressurized, and the resultant partially and completely fluorinated benzotrifluorides were removed from the reaction mixture by distillation. The resultant distillate was analyzed by gas chromatography. The results can be seen in Table 1. Tetrafluorobenzotrifluoride was obtained in purified form from the distillate by fractional distillation.

Example 6

Inventive Preparation of Tetrafluorobenzotrifluoride

The procedure of Example 5(a) was followed, but the catalyst was 6.6 g of N-(N,N-dimethylimidazolidino)tris(diethylamino)phosphazenium chloride and, instead of dichloromethane, 28 g of sulfolane were used. In addition, in substep (b) the mixture was only heated for 24 hours at 200° C. The analytical results after carrying out steps (a) and (b) can be seen in Table 1.

Example 7

Inventive Preparation of Tetrafluorobenzotrifluoride

The procedure of Example 5(a) was employed, but the catalyst was 8.24 g of diethylaminobis(tetramethylguanidino)sulfonium bromide, and in step (b) the mixture was heated for only 24 hours at 200° C. The analytical results obtained after carrying out substeps (a) and (b) can be seen in Table 1.

Comparison Example 6

Preparation of Tetrafluorobenzotrifluoride According to the Prior Art

The procedure of Example 5(a) was followed, but the catalyst was 8.38 g of tetraphenylphosphonium bromide, and in substep (a) the mixture was heated for 28 hours at 200° C. The analytical results obtained after carrying out substeps (a) and (b) can be seen in Table 1.

TABLE 1

| | Contents of halogenated benzotrifluorides (BTF), figures in % | | | | |
|---|---|---|---|---|---|
| | Tetrachloro-BTF | Trichloromonofluoro-BTF | Dichlorodifluoro-BTF | Monochlorotrifluoro-BTF | Tetrafluoro-BTF |
| after substep (a) | | | | | |
| Example 5 | 0 | 21 | 66 | 0 | 0 |
| Example 6 | 0 | 5 | 70 | 24 | 1 |
| Example 7 | 4 | 51 | 44 | 1 | 0 |
| Comparative Example 6 | 19 | 62 | 19 | 0 | 0 |
| after substep (b) | | | | | |
| Example 5 | 0 | 0 | 0 | 17 | 84 |
| Example 6 | 0 | 0 | 0 | 33 | 67 |
| Example 7 | 0 | 0 | 0 | 35 | 65 |
| Comparative Example 6 | 0 | 14 | 78 | 6 | 1 |

Example 8

Inventive Preparation of N-(N,N-dimethylimidazolidino)tris(diethylamino-phosphonium)chloride, Formula (VI))

282.9 g of phosphorus pentachloride in 1000 ml of dichloromethane were placed under an inert gas atmosphere in a 4 liter 3-neck flask equipped with anchor stirrer, dropping funnel, and gas inlet tube and 730 g of diethylamine were added in portions at −30° C. Appropriate cooling ensured that the temperature did not exceed −15° C. After addition was complete, the reaction mixture was allowed to warm up to room temperature and was then stirred for a further 2 hours. Then, at 0° C., 30 g of ammonia were introduced, and the mixture was again allowed to warm up to room temperature and was further stirred for 2 hours at room temperature. All volatile constituents of the reaction mixture were then taken off in vacuo and the residue was dissolved in a mixture of 350 ml of water and 550 g of 40% strength by weight of aqueous sodium hydroxide solution. After the mixture was stirred for one hour at room temperature, ammonia, diethylamine, and water were separated by distillation and a residue was obtained that essentially comprised $(ethyl_2N)_3P—NH_2^+Cl^-$ and sodium chloride. 2800 ml of 50% strength by weight aqueous sodium hydroxide solution were added and extraction with toluene produced $(ethyl_2N)_3P=NH$ in 85% yield.

This material (131 g) was added in portions at −10 to −20° C. to a solution of 42.2 g of 2-chloro-1,3-dimethylimidazolinium chloride in 250 ml of dichloromethane. The mixture was then stirred for 4 hours at 0° C. and for 2 hours at room temperature. The solvent was then removed in vacuo, the residue was suspended in 300 ml of methanol, and 18.4 g of potassium methoxide dissolved in 100 ml of methanol were added at −20° C. The reaction mixture was allowed to warm to room temperature and was filtered and the solvent was taken off from the filtrate. This produced N-(N,N-dimethylimidazolidino)tris(diethylaminophosphonium)chloride in 93% purity.

Melting point: 64 to 65° C.

$^1$H-NMR (200 MHz, CDCl$_3$): δ=0.69 (t, $^3J_{H\text{-}H}$=6.9H, 18H, CH$_3$CH$_2$N), 2.49 (s, 6H, CH$_3$N), 2.65 (dq, $^3J_{H\text{-}H}$=6.9 Hz, $^3J_{H\text{-}H}$=10.7 Hz, 12H, CH$_2$CH$_2$) $^{31}$P-NMR (80 MHz, decoupled): δ=19.1 (s) $^{13}$C-NMR (50.3 MHz, CDCl$_3$): δ=13.2 (s, CH$_3$, CH$_3$CH$_2$N), 33.3 (s, CH$_3$, CH$_3$N), 39.4 (s, CH$_3$, CH$_3$CH$_2$N), 47.3 (s, CH$_2$, CH$_2$CH$_2$), 155.6 (d, C=N, $^2J_{C\text{-}P}$=25.1 Hz)

Example 9

Inventive Preparation of Diethylaminobis(tetramethylguanidino)sulfonium bromide, Formula (VII))

Under an inert gas atmosphere, 7.5 g of bromine were added dropwise at −35° C. to a solution of 8.85 g of bis(diethylamino)sulfide in 40 ml of dichloromethane. After the addition the mixture was further stirred for 30 minutes at −35° C. and then 11.5 g of tetramethylguanidine were added dropwise. The mixture was allowed to warm to room temperature, further stirred for 1 hour, and then cooled to 0° C. At this temperature, 2.8 g of sodium ethoxide (dissolved in 50 ml of methanol) were added and the mixture was then allowed to come to room temperature. Methanol was taken off in vacuo at 20 to 100° C. and the residue was washed with pentane. This produced 17.6 g of a 4:1 mixture of diethylaminobis(tetra-methylguanidino)sulfonium bromide with bisdiethylamino(tetramethyl-guanidino)sulfonium bromide. Recrystallization from acetone/diethyl ether produced 8.5 g (41.3% of theory) of diethylaminobis(tetramethylguanidino)sulfonium bromide in pure form.

Melting point: 117 to 119° C. $^{13}$C-NMR (50.3 MHz, CDCl$_3$): δ=14.5 (CH$_3$, CH$_3$CH$_2$N), 41.1 (CH$_3$, CH$_3$N), 41.7 (CH$_2$, CH$_3$CH$_2$N).

Example 10

Inventive Preparation of Tris(tetramethylguanidino)sulfonium chloride 10 g of sulfur dichloride in 100 ml of dichloromethane were introduced under an inert gas atmosphere at −78° C. and 3.4 g of chlorine gas were condensed into the mixture. 69.0 g of tetramethylguanidine were then added and the mixture was allowed to warm up slowly to room temperature. The solvent was removed in vacuo and the residue was cooled to 0° C. At this temperature, 5.8 g of sodium methoxide dissolved in 40 ml of methanol were added and the mixture was then allowed to warm up to room temperature. The methanol was taken off in vacuo. This produced tris(tetramethylguanidino)sulfonium chloride in 97% yield and 96.5% purity.

Melting point: 115 to 116° C. $^1$H-NMR (200 MHz, CDCl$_3$): δ=2.83 (s, 18H, CH$_3$N) $^{13}$C-NMR (50.3 MHz, CDCl$_3$): δ=40.9 (CH$_3$, CH$_3$N), 165.0 (C=N)

Example 11

Inventive Preparation of diethylaminobis[tris(diethylamino)phosphazenyl]-sulfonium bromide, Formula VIII))

5.0 g of bromine were added dropwise under an inert gas atmosphere at −35° C. to a solution of 5.7 g of bisdiethylamino sulfide in 25 ml of dichloromethane. After addition was completed, the mixture was further stirred for 30 minutes at this temperature and 7.2 g of tris(diethyl-amino) phosphazene were then added. The mixture was allowed to warm to room temperature and was stirred for a further one hour and then cooled to 0° C. again. At this temperature, 1.8 g of sodium methoxide dissolved in 40 ml of methanol were added and the mixture was then allowed to warm up to room temperature. The methanol was taken off in vacuo and the residue was washed twice with pentane. This produced a 4:1 mixture of diethylaminobis[tris(diethylamino)phosphazenyl]-sulfonium bromide with bis(dimethylamino)trisdiethylamino)phosphazenylsulfonium bromide.

$^{31}$P-NMR (80 MHz, decoupled): 38.4 (s, 20%), 32.7 (s, 80%).

What is claimed is:

1. A process for preparing nuclear-fluorinated aromatics comprising reacting, at 40 to 260° C., (1) an aromatic compound substituted at the nucleus with halogen that is exchangeable for fluorine, with (2) a fluoride, in the presence of (3) at least one compound of the formula (I),

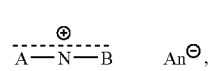
(I)

where

A is a radical of the formula (II) or (III)

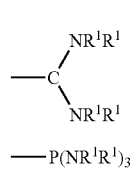

and

B independently of A is a radical of the formula (II), (III), (IV), or (IVa)

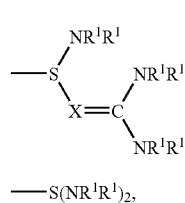

where the individual $R^1$ are identical or different and are each unbranched or branched $C_1$-$C_{10}$ alkyl, unbranched or branched $C_2$-$C_{10}$ alkylene, or $C_6$-$C_{12}$ aryl, where one or more $NR^1R^1$ groups can also be a 3- to 7-membered saturated or unsaturated ring that is formed from a nitrogen atom, the remainder of the ring atoms being carbon atoms, and where the radical of the formula (II) and the

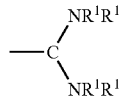

group in formula (IV) can also be the radical of a saturated or unsaturated 4- to 8-membered ring that contains two nitrogen atoms, the remainder of the ring atoms being carbon atoms, X is nitrogen or phosphorus, and $An^\ominus$ is one equivalent of an anion.

2. A process according to claim 1 wherein the radicals $R^1$ are methyl, ethyl, propyl, or butyl, or an $NR^1R^1$ group is a 5- to 7-membered saturated or unsaturated ring that is formed from one nitrogen atom, the remainder of the ring atoms being carbon atoms, or the radical of the formula (II) or the

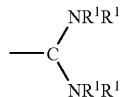

group in formula (IV) is a saturated 5- or 7-membered ring that contains two nitrogen atoms, the remainder of the ring atoms being carbon atoms; X is nitrogen; and $An^\ominus$ is chloride, bromide, $(CH_3)_3SiF_2^\ominus$, $HF_2^\ominus$, $H_2F_2^\ominus$, tetrafluoroborate, hexafluorophosphate, carbonate, or sulfate.

3. A process according to claim 1 for preparing a nuclear-fluorinated aromatic of the formula (X)

where $R^2$ independently of one another are each F, Cl, Br, $NO_2$, CN, $CF_3$, $CCl_3$, CHO, $OCF_3$, $SCF_3$, $COR^4$, $COOR^4$, COY, or $SO_2Y$, where $R^4$ is $C_{1-10}$ alkyl and Y is F, Cl, Br or CF3, $R^3$ independently of one another are each hydrogen or an unbranched or branched $C_1$-$C_{10}$ alkyl or $C_1$-$C_{10}$ alkoxy radical, Ar is an aromatic or heteroaromatic radical having a total of 6 to 10 ring atoms, where the ring atoms are only carbon atoms or alternatively are carbon atoms plus 1 to 3 heteroatoms selected from the group consisting of nitrogen, oxygen, and sulfur, x is an integer from 1 to 3, w is an integer from 1 to y, y is an integer from 1 to 5, and z is zero or an integer from 1 to 5, where the total x+y+z equals the number of all substitutable valencies on the radical Ar, wherein the aromatic compounds substituted with halogen that are exchangeable for fluorine correspond to the formula (XI)

where $R^2$, $R^3$, Ar, x, y, and z have the meanings specified for formula (X).

4. A process according to claim 3 wherein in the formulas (X) and (XI)

$R^2$ independently of one another are each Cl, $NO_2$, CN, $CF_3$, COCl, or CHO, $R^3$ independently of one another are each hydrogen, methyl, ethyl, methoxy, or ethoxy, Ar is a phenyl or pyridyl radical, x is 1 or 2, w is 1 or 2, y is an integer from 1 to 4, and z is zero or 1.

5. A process according to claim 1 wherein 0.001 to 0.5 mol of one or more compounds of the formula (I) and 0.8 to 2 equivalents of one or more fluorides are used per 1 mol of halogen that is bound to the nucleus of the aromatic compound and is to be exchanged for fluorine.

6. A process according to claim 1 carried out in the presence of a dipolar aprotic solvent and/or nonpolar aprotic solvent.

7. A process according to claim 1 wherein a solvent is not used for the conversion of a polychlorinated benzotrifluoride to a fluorinated and chlorinated benzotrifluoride and/or to a polyfluorinated benzotrifluoride.

8. A process for preparing a compound of the formula (I)

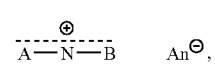

where

A is a radical of the formula (II) or (III)

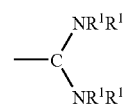

and

B independently of A is a radical of the formula (II), (III), (IV), or (IVa)

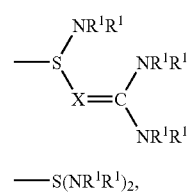

where the individual $R^1$ are identical or different and are each unbranched or branched $C_1$-$C_{10}$ alkyl, unbranched or branched $C_2$-$C_{10}$ alkylene, or $C_6$-$C_{12}$ aryl, where one or more $NR^1 R^1$ groups can also be a 3- to 7-membered saturated or unsaturated ring that is formed from a nitrogen atom, the remainder of the ring atoms being carbon atoms, and where the radical of the formula (II) and the

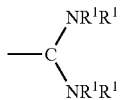

group in formula (IV) can also be the radical of a saturated or unsaturated 4- to 8-membered ring that contains two nitrogen atoms, the remainder of the ring atoms being carbon atoms, X is nitrogen or phosphorus, and $An^{\ominus}$ is one equivalent of an anion, comprising (a) reacting (i) a compound of the formula $$[A\text{-}An']^{\oplus} An^{\ominus} \quad \text{(XII),}$$

where

A has the meaning specified for formula (I) or corresponds to the formula (IVa), An' is chlorine or bromine and $An^{63}$ is one equivalent of an anion, with (ii) a compound of the formula (XIII)

$$HN=A' \quad \text{(XIII),}$$

where

A' with respect to the arrangement of the atoms has the meaning specified for A of formula (I) but is double-bonded, and (b) adding a base.

9. A process according to claim 8 wherein the base is an alkoxide, a tertiary amine, or an excess of a compound of the formula (XIII) in an amount of 1 to 1.2 equivalents per 1 mol of the compound of the formula (XII).

10. A process according to claim 8 carried out at −80° C. to +70° C. using 0.8 to 3 mol of a compound of the formula (XIII), based on the compound of the formula (XII), wherein the base is added at −50 to +40° C.

* * * * *